United States Patent [19]

Swartz

[11] Patent Number: 4,932,935
[45] Date of Patent: * Jun. 12, 1990

[54] ASSISTED LIPECTOMY DEVICE

[76] Inventor: Barry Swartz, 8070 Pimlico La., Boerne, Tex. 78006

[*] Notice: The portion of the term of this patent subsequent to Apr. 5, 2005 has been disclaimed.

[21] Appl. No.: 123,176

[22] Filed: Nov. 20, 1987

Related U.S. Application Data

[63] Continuation-in-part of Ser. No. 907,505, Sep. 15, 1986, Pat. No. 4,735,605.

[51] Int. Cl.$^5$ .............................................. A61B 17/00
[52] U.S. Cl. ....................................... 604/22; 604/902; 606/171
[58] Field of Search ................. 604/22, 902, 264, 267; 128/303 R, 305, 755, 311; 74/89.15; 30/29.5, 263-265, 387; 433/110

[56] References Cited

U.S. PATENT DOCUMENTS

| 3,082,805 | 3/1963 | Royce | 146/68 |
| 3,732,858 | 5/1973 | Banko | 128/2 B |
| 3,955,579 | 5/1976 | Bridgman | 128/304 |
| 4,167,944 | 9/1979 | Banko | 128/305 |
| 4,203,444 | 5/1980 | Bonnell | 128/276 |
| 4,311,140 | 1/1982 | Bridgman | 128/276 |
| 4,735,605 | 4/1988 | Swartz | 128/305 |

OTHER PUBLICATIONS

Ricardo Baroudi, M.D., "Body Sculpturing", Clinics in Plastic Surgery-vol. 11, No. 3, Jul. 1984.
Yves-Gerard Illouz, M.D., "Illouz's Technique of Body Contouring by Lipolysis"-Clinics in Plas. Surg.-vol. 11, No. 3, 7/84.
U. K. Kerselring, M.D., "Body Contouring with Suction Lipectomy", Clinics in Plas. Surg.-vol. 11, No. 3, 7/84.

Primary Examiner—John D. Yasko
Assistant Examiner—J. L. Kruter

[57] ABSTRACT

An improved lipectomy device, or cannula, is disclosed having inner and outer tubes. The outer tube has an elongated aspiration aperture, and the inner tube has a spiral slot. A mechanism inside the handle of the device causes the inner tube to rotate, creating a traveling hole effect along the aspiration aperture. Alternatively, the inner tube may oscillate rather than complete full rotations. This obviates the necessity of the surgeon repeatedly pushing the cannula in and out.

19 Claims, 3 Drawing Sheets

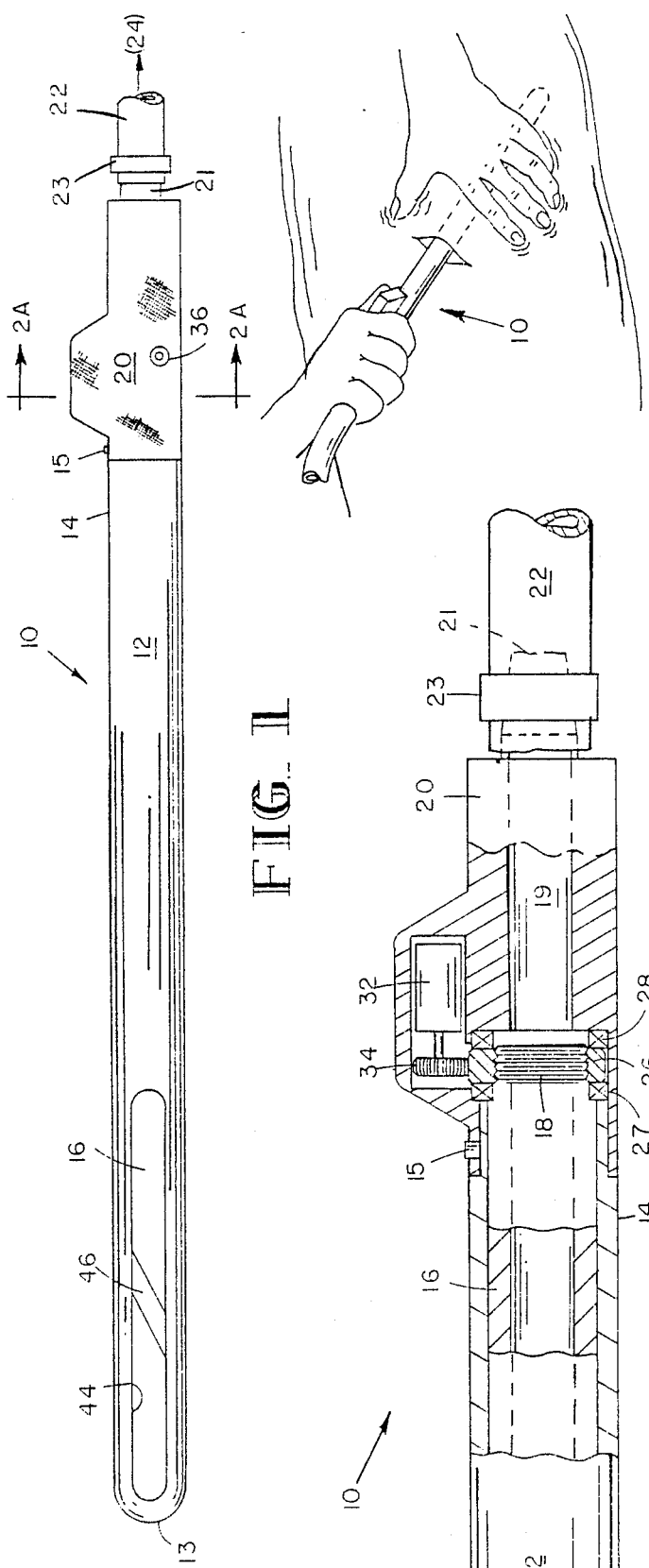
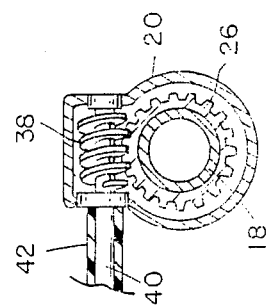

ASSISTED LIPECTOMY DEVICE

CROSS-REFERENCES TO RELATED APPLICATIONS

The present application is a continuation-in-part of U.S. patent application Ser. No. 907,505 for an Assisted Lipectomy Device, filed Sept. 15, 1986 now U.S. Pat. No. 4,735,605.

BACKGROUND OF THE INVENTION

1. Field of the Invention

The present invention relates to a lipectomy device for removing unwanted fat, and more particularly to a motorized improvement of such a device.

2. Description of the Prior Art

Body sculpturing, or body contour surgery, is a routine procedure used to increase the attractiveness of the human form. One particular technique of body sculpturing involves suction lipectomy, also known as liposuction or lipexheresis (Greek for "fat suction").

This technique was first used in Europe by J. Schrudde in 1972, who used a uterine curet for this purpose. Such a curet is depicted in U.S. Pat. No. 3,955,579, issued to Bridgman on May 11, 1976. An improved curet is shown in U.S. Pat. No. 4,311,140, also issued to Bridgman, on Jan. 19, 1982.

Although this technique was first treated with some apprehension, it has now become widely accepted by both the medical community and by the layman. It can be practiced by physicians with different backgrounds, e.g., general practitioners, dermatologists, otorhinolaryngologists, or gynecologists, although it is most often performed by plastic surgeons. It has been used to remove fat from all over the body. The regions most frequently treated include the trochanteric region, flanks, buttocks, inner aspect of the knee, the anterior abdominal wall, gynecomastia, and "lovehandles." Although it was once believed that the fat cells so removed would later be replaced, the present accepted theory is that the body contains a limited number of fat cells that cannot regenerate. Fatty tissue is thus caused not by an increase in the number of fat cells, but by an increase in the amount of lipid matter found within the cell boundaries. Therefore, it is thought that removal of the fat cells by liposuction will create a contour that will retain its form.

Today the procedure is performed using a special type of curet known as a cannula. One excellent article discussing various shapes and sizes of cannulas is "Body Contouring with Suction Lipectomy" by Kesselring, published in *Clinics in Plastic Surgery*, Vol. 11, No. 3 (July 1984). One cannula often used is known as the Aspiradeps, manufactured by Ulrich A. G., in St. Gall, Switzerland. The cannula is attached to a vacuum source which carries away the fat tissue. The vacuum pressure is usually on the order of 0.4 to 0.6 atmospheres.

There are two accepted techniques practiced today. The first is the tunneling procedure proposed by Illouz. In this method, one or two incisions are made, with radial excursions of the instrument into the flesh. The result is a multitude of concomitant sinuses. The second, and most common method, is the original liposuction procedure proposed by Kesselring. In that technique, an entire layer of regular, deep fat is removed, leaving a smooth, deep surface of the residual panniculus. The space thus created is then compressed, optionally followed by skin retraction.

Both of these techniques require that the surgeon push and pull the entire cannula back and forth about twenty times for each incision made. Normally, twenty to thirty incisions, or tunnels, are made. This is necessary to insure even removal of fat in the targeted region. The surgeon typically massages the flesh in the area of the aperture in the cannula, while at the same time thrusting the rod in and out of the tunnel. This is an extremely traumatic method, both for the patient and the doctor. The patient's flesh turns black and blue for several days. Moreover, many surgeons practicing this technique find it physically exacting, and most come out of the operating room extremely tired. It would therefore be desirable and advantageous to devise an improved cannula which would assist the surgeon in the lipectomy procedure, decreasing the amount of trauma to the tissues and decreasing the physical exertion expended by the surgeon.

SUMMARY OF THE INVENTION

Accordingly, the primary object of the present invention is to provide an improved lipectomy device which will assist the surgeon in the removal of fat from surrounding tissue.

Another object of the invention is to provide such a device which will reduce general trauma to the tissue of the patient.

Yet another object of the invention is to provide such a device which will reduce localized trauma to blood vessels, nerves, skin, muscles, and lymphatic tissue of the patient.

Still another object of the invention is to provide such a device that will allow minimal scarring, minimal pain and discomfort, minimal risks, and a faster recovery period.

The foregoing objects are achieved in an assisted lipectomy device having an outer tube with a longitudinal slot, and an inner rotating tube with a spiral slot, whereby a "traveling hole" is created which may more effectively remove fatty tissue. The inner tube may oscillate rather than fully rotate.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

FIG. 1 is a side elevational view of the improved cannula of the present invention.

FIG. 2 is a partial cross-section of the cannula of the present invention showing the attachment of the inner and outer tubes to the gear assembly and handle.

FIG. 2A is a cross-section of the cannula of the present invention taken along lines 2A—2A of FIG. 1 showing an alternative gear assembly.

FIG. 3 is a partial cross-section of the cannula of the present invention showing the interaction of the spiral slot of the inner tube and the longitudinal slot of the outer tube.

FIG. 3A is a cross-section of the tip of the cannula taken along lines 3A—3A of FIG. 3.

FIG. 4 is a perspective view of the improved cannula of the present invention depicting actual use of the device.

DESCRIPTION OF THE PREFERRED EMBODIMENTS

Figure 5:
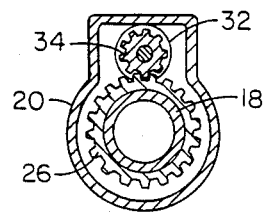
FIG. 5 is a cross-section of the cannula depicting the bevel gear motor device.

With reference now to the figures, and in particular with reference to FIG. 1, there is depicted a side view of the improved cannula 10 of the present invention. Improved cannula 10 comprises an outer tube 12, an inner tube 16, a handle 20, and a hose 22 leading to a vacuum source 24 (not shown). Cannula 10 may be any length up to 45 cm., but it generally depends on the location of the fat deposits. A 30 cm. cannula is preferred for the larger areas such as the buttocks, hips, and "saddlebags (upper thighs)." A 10 cm. cannula is preferred for the knees, ankles, abdomen, and arms, and a 5 cm. or smaller cannula is required for the face. The diameter of the cannula is likewise variable, generally within the range of five to twenty-five millimeters. The distal end 13 of outer tube 12 should be slightly rounded or bullet-shaped. If the end were pointed or sharp, it might puncture vital organs or blood vessels within the body. If the end were totally flat, it would cause excessive damage to the fatty tissues. Handle 20 is preferably made of a resilient material, such as metal or hard plastic. Integral with handle 20 is port 21. Hose 22 is attached to port 21 by means of clamp 23, and should be made of a clear plastic.

With further reference to FIG. 2, it can be seen that inner tube 16 rotates within fixed outer tube 12 by means of a tube gear 26. The proximate end 14 of outer tube 12 is attached to handle 30 by means of a conventional twist and lock arrangement 15. The proximate end 18 of inner tube 16 is threaded and engages with inner tube gear 26. Tube gear 26 is held in place by bearings 27 and 28.

One advantage of this attachment method is the interchangeability of different sizes of inner and outer tubes. Although most cannulas tody are made of surgical steel, it is envisioned that the outer and inner tubes 12 and 16 may be made of hard plastic or other easily manufactured material so as to make them disposable. The surface of inner tube 16 may be coated with an anti-friction compound such as Teflon to ease the rotation thereof within outer tube 12.

Two alternate means of driving tube gear 26 are contemplated. The first, depicted in FIG. 2, includes an electric motor 32 housed within handle 20. Motor 32 would require a power cord (not shown) for connection to a source of electricity. Motor 32 powers drive gear 34 which in turn engages tube gear 26. Motor 32 may be activated by a thumb-operated on/off switch 36. Motor 32 may be air-driven instead of electric.

The second, and preferred, driving means is shown in FIG. 2A. This consists of a worm gear 38 engaged with tube gear 26. Worm gear 38 is powered by a rotating steel cable 40, located within a protective sheath 42. Cable 40 is powered by remote motor means, and controlled by a foot pedal (not shown). An example of such an arrangement is the cable system manufactured by Dermatomes for use with the skin grafts. In this embodiment, element 36 may simply be a dimple for the thumb so that the operator is aware of the orientation of cannula 10.

Figure 3B:
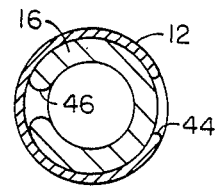
FIG. 3B is similar to FIG. 3A, but it more clearly shows the rounded edges of the slots.

With reference now to FIGS. 3 and 3A, it can be seen that both outer and inner tubes 12 and 16 are hollow. Outer tube 12 has a longitudinal slot 44 which generally corresponds to the aspiration apertures of the prior art cannulas. However, longitudinal slot 44 in much longer than those apertures. Although slot 44 may extend the entire length of outer tube 12, it is preferred, for reasons discussed below, that its length be approximately the width of a normal human hand, or about 8 cm., and begin near the distal end 13 of outer tube 12. It should be at least 4 cm. long. The width of slot 44 should be between three and twenty millimeters, and preferably about 5 mm.

Inner tube 16 has a spiral slot 46 located near its distal end 17 so as to coincide with longitudinal slot 44 of outer tube 12. The effective length of spiral slot 46 should correspond to the length of longitudinal slot 44. Spiral slot 46 may make several revolutions around inner tube 16, but it is preferred that spiral slot 46 make only one 360° rotation along this length. Thereby, when inner tube 16 rotates, a "traveling hole" appears in longitudinal slot 44. The width of spiral slot 46 may be between three and twenty millimeters, preferably 12 mm. This feature obviates the necessity of the surgeon repeatedly pushing the cannula 10 to and fro, facilitating the entire operation and minimizing discomfort to the patient.

The direction of rotation of inner tube 16 should complement the threading of proximate end 18, so as to keep inner tube 16 engaged with tube gear 26. If proximate end 18 has right-handed male threads, the direction of rotation of inner tube 16 is counterclockwise as shown in FIG. 3A.

In the preferred embodiment, the edges of longitudinal slot 44 and spiral slot 46 are rounded rather than sharp. The functional differences between a rounded edge and a sharp edge are only apparent in the way in which the fat lobules are removed from their nutrient vessels. With the rounded edge, the fat lobules are torn off (avulsion) by the suction power across the edge of the slot, with minimal damage to the nutrient vessels; with a sharp edge, they are cut off (section) while being sucked into the tube. With the latter device, there exists a chance that the nutrient vessels themselves, or nerves or lymphatic tissue, may be cut, which is obviously undesirable. The fat will then be conveyed down the center of inner tube 16, through cavity 19 in handle 20, and out port 21 and hose 22.

In an equivalent embodiment, the locations of the spiral and longitudinal slots could be reversed, placing the spiral slot on outer tube 12 and the longitudinal slot on inner tube 16. This approach, however, has certain drawbacks. First of all, the "traveling hole" would rotate around the cannula, making it impossible to concentrate on a given layer of fat. This would also result in excessive trauma to the surrounding tissue, and require a more powerful motor. Alternately, the inner tube may be similar to a piston, and have an annular slot which would slide along the inside of the longitudinal slot.

A further alternative embodiment, which is the subject of this continuation-in-part application, is shown in FIGS. 6-10. In this embodiment, inner tube 16 oscillates back and forth rather than completing full rotations. Thus the traveling hole created runs up and down longitudinal slot 44 rather than disappearing at one end and reappearing at the other. This design may be superior to full rotation of inner tube 16 since it avoids pinching off tissue when the traveling hole disappears.

Figure 7:
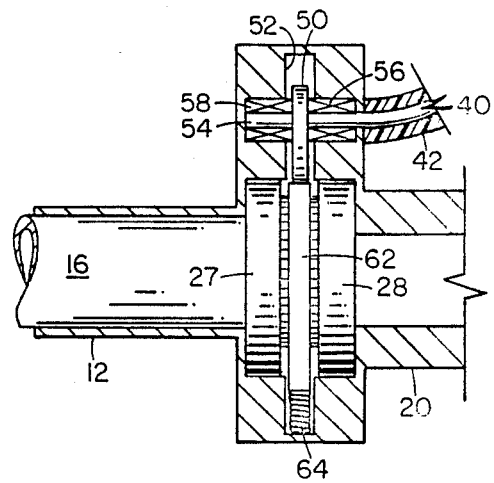
FIG. 7 is a top plan view taken along lines 7—7 of FIG. 6.

In the preferred version of this embodiment, an external motor (not shown) provides rotational torque to a cable 40 as in FIG. 2A. However, as shown in FIG. 7, cable 40 and sheath 42 enter handle 20 parallel to handle 20, rather than perpendicular as shown in FIG. 2A. This is required for the rack and pinion drive used in the oscillation embodiment, which is now explained.

Figure 6:
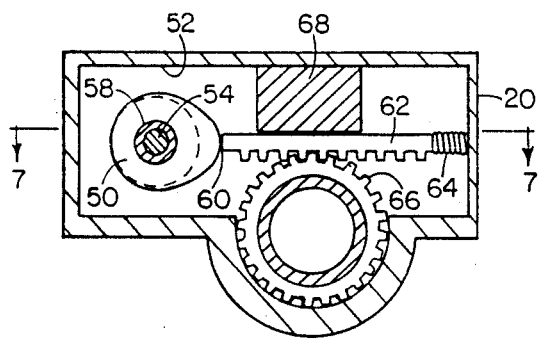
FIG. 6 is a cross-section similar to FIGS. 2A and 5, but FIG. 6 shows the cam-actuated rack and pinion system for oscillation of the inner tube.

With reference to FIGS. 6 and 7, cable 40 enters handle 20 and connects directly to a cam disk 50. Cam disk 50 is secured to the inner wall 52 of handle 20 by any convenient means, such as an axle 54 and sleeve bearings 56 and 58. Cam disk 50 is free to make complete rotations within handle 20. A lobe 60 is attached to and integral with cam disk 50, which interacts with a rack 62, lying in the same plane as cam disk 50. Rack 62 is further secured to inner wall 52 of handle 20 by biasing means 64, which urges rack 62 toward cam disk 50. The tube gear 26 of FIG. 5 has now become a pinion 66, which engages rack 62. Thus, as cable 40 and cam disk 60 rotate, rack 62 is pushed left and right as viewed in FIG. 6. This in turn causes inner tube 16 to oscillate, rather than completely rotating. The oscillatory motion of inner tube 16 is achieved whether cable 40 rotates in a clockwise or counterclockwise direction. Guide member 68 helps keep rack 62 forced against pinion 66.

Figure 8:
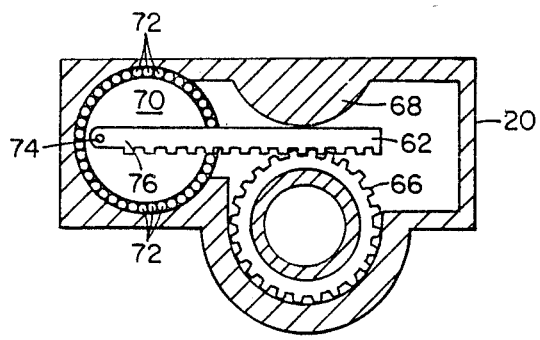
FIG. 8 is like FIG. 6 but it shows a crank-actuated rack and pinion system.

A second version of the rack and pinion embodiment is shown in FIG. 8. In this embodiment, rack 62 is actuated by a crank assembly rather than by a camming action. Cable 40 is again attached to a disk, but now it is a simple circular disk 70. Circular disk 70 is held in place by means of roller bearings 72. A pin 74 is attached to the periphery of circular disk 70. The pin 74 is essentially perpendicular to circular disk 70. Rack 62 is rotatably mounted to pin 74. Rack 62 may have a crank arm 76 for this purpose. Thus, as circular disk 70 rotates, rack 62 is again pushed to the left and right. Guide member 68 is now rounded to allow for the variable orientation of rack 62 as it moves.

It is understood that the essence of the present invention lies in the ability of inner tube 16 to oscillate, and that the above embodiments are merely two arrangements that perform this function. The same object may be achieved in the embodiment shown in FIGS. 2 and 5 if the motor 32 is a servomechanism designed to switch drive directions after advancing gear 34 a short interval.

Figure 10:
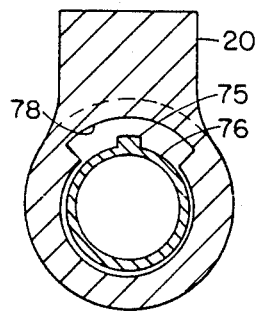
FIG. 10 is a cross-section along lines 10—10 of FIG. 9.
Figure 9:
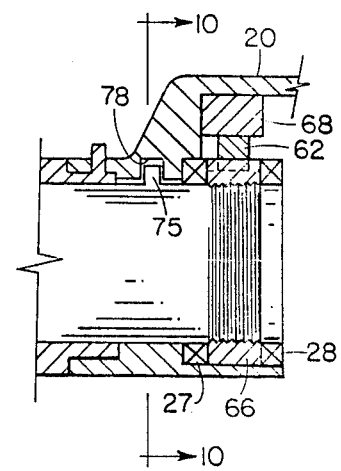
FIG. 9 is a cross-section similar to FIG. 2 showing the tab and groove used to limit oscillation of the inner tube.

A further refinement of the oscillating cannula is shown in FIGS. 9 and 10. If the rotation of inner tube 16 is not properly limited, then spiral slot 46 may become misaligned with longitudinal slot 44. For example, if inner tube 16 rotates 180° during a given half-cycle of oscillatory motion, then spiral slot 46 will be located only along one side of inner tube 16. In this case, if inner tube 16 is not properly oriented with respect to the longitudinal slot 44 on outer tube 12, for whatever reason (such as improper initial assembly or a hysteresis in servomechanism 32), then spiral slot 46 will not even appear through longitudinal slot 44, i.e., the cannula will be nonfunctional. In order to prevent such an occurrence, inner tube 16 may be provided with a tab 75 along its outer surface 76 which fits inside a guide channel 78 cut inside handle 20. Tab 75 thereby limits rotational movement of inner tube 16, insuring that spiral slot 46 will always be properly aligned with longitudinal slot 44.

OPERATION

Existing procedures for preparing the patient for the lipectomy may be used in operations employing the improved cannula 10. The regions to be suctioned should be demarcated depending on the technique to be used. Anesthesia can be general, peridural, or local. The patient should be in either the prone or supine position depending on the targeted area. A saline or distilled water solution may be infiltrated in the fatty deposits.

An incision is made in the skin from 5 to 20 mm. in length depending on the diameter of the cannula. The device 10 is then inserted into the incision, creating a tunnel at the deep level of the tissue, near the fascia. This is necessary to avoid the lymphatics contained in the subcutaneous fat, and to retain skin trophicity and tonicity. The vacuum source 24 is then activated. A negative pressure of 0.3 to 1.5 atm. is required, depending on the size of the slots 44 and 46. It is anticipated that the optimum negative pressure for a cannula having an longitudinal slot width of 6 mm. and a spiral slot width of 12 mm. would be 1.0 atm.

When the cannula 10 is in place and the vacuum is turned on, the operator should activate the rotation or oscillation of inner tube 16 by using the foot pedal, in the case of the preferred rack and pinion mechanism, or by depression of switch 36 in the case of the motor 32 within handle 20. As depicted in FIG. 4, the operator should then begin to gently massage the region. The aspirated fat will be seen in hose 22. Fat is pure yellow, and if blood appears in the tubing the operator should change the orientation of cannula 10, or remove it. Filter units (not shown) may be attached to hose 22 before the vacuum source to keep track of the amount of fat and blood removed. After 100 cc. of fat have been removed, a new tunnel should be made and the procedure repeated. It is advisable to remove no more than six pounds of fatty tissue in order to avoid shock and other complications.

When the removal is complete, compression bandages should be applied. More than one operation may be necessary. Skin retraction may follow.

Although the invention has been described with reference to specific embodiments, this description is not meant to be construed in a limiting sense. Various modifications of the disclosed embodiments, as well as alternative embodiments of the invention will become apparent to persons skilled in the art upon reference to the description of the invention. It is therefore contemplated that the appended claims will cover such modifications that fall within the true scope of the invention.

I claim:

1. An assisted lipectomy device, comprising:
   handle means;
   an outer tube having distal and proximate ends, and having a longitudinal slot, said outer tube being open at said proximate end, and said proximate end of said outer tube attached to said handle means;
   an inner tube having distal and proximate ends, and having a spiral slot, said inner tube located within said outer tube, said inner tube being open at said proximate end, and said proximate end of said inner tube attached to said handle means;

said spiral and longitudinal slots each having rounded edges;

motor means coupled to said inner tube for oscillating said inner tube; and vacuum means for creating suction within said inner tube.

2. The assisted lipectomy device of claim 1 wherein said motor means comprises:
a motor remote from said handle means;
a flexible steel cable having a first end and a second end, said first end rotatably connected to said motor; and
means coupling said second end of said cable to said inner tube, whereby rotation of said cable causes said inner tube to oscillate.

3. The assisted lipectomy device of claim 2 wherein said coupling means includes:
rack means operatively connected to said second end of said cable; and
pinion means operatively connected to said proximate end of said inner tube, said pinion means engaging said rack means, whereby lateral movement of said rack means causes rotational movement of said pinion means.

4. The assisted lipectomy device of claim 3 wherein said second end of said cable is attached to a cam disk, said cam disk being generally parallel to and in contact with said rack means, and further including means for biasing said rack means toward said cam disk.

5. The assisted lipectomy device of claim 3 wherein said second end of said cable is attached to an essentially circular disk, said cable being generally perpendicular to said circular disk, and said circular disk being generally parallel to said rack means, said rack means further being pivotally connected to the periphery of said circular disk.

6. The assisted lipectomy device of claim 1 further comprising:
a tube gear surrounding said proximate end of said inner tube;
a drive gear for engagement with said tube gear; and
a servomechanism coupled to said drive gear for alternately rotating said drive gear clockwise and counterclockwise.

7. The assisted lipectomy device of claim 1 further comprising means for limiting oscillation of said inner tube.

8. The assisted lipectomy device of claim 7 wherein said limiting means comprises a tab attached to an outer surface of said inner tube near said proximate end thereof, said tab positioned within a groove in said handle means.

9. An assisted lipectomy device comprising:
a hollow handle having first and second ends, and having means for attaching said handle to a vacuum source;
an inner tube having distal and proximate ends, said proximate end of said inner tube passing through said first end of said handle and having a tube gear attached thereto, said inner tube further having a spiral slot with rounded edges;
an outer tube having distal and proximate ends and surrounding said inner tube, said proximate end of said outer tube being attached to said first end of said handle and having a longitudinal slot with rounded edges; and motor means coupled to said tube gear for imparting oscillatory motion to said inner tube.

10. The assisted lipectomy device of claim 9 wherein said motor means comprises:
a motor remote from said handle;
a flexible steel cable having first and second ends, said first end rotatably connected to said motor; and
means for operatively connecting said second end of said cable to said tube gear, whereby rotation of said cable causes said inner tube to oscillate.

11. The assisted lipectomy device of claim 10 wherein said tube gear forms a pinion, and said means for operatively connecting said second end of said cable to said tube gear includes a rack coupled to said second end of said cable, said rack engaging said pinion whereby lateral movement of said rack causes rotational movement of said pinion.

12. The assisted lipectomy device of claim 11 wherein said second end of said cable is attached to a cam disk, said cam disk being generally parallel to said rack, said cam disk having a lobe along its periphery, said rack slidably engaging said periphery of said cam disk, and further including means for biasing said rack toward said cam disk whereby, as said rack oscillates laterally, said pinion and said inner tube oscillate rotationally.

13. The assisted lipectomy device of claim 11 wherein said second end of said cable is attached to an essentially circular disk, said circular disk being generally parallel to said rack, said rack further being pivotally connected to the periphery of said circular disk.

14. The assisted lipectomy device of claim 13 further comprising means for limiting oscillation of said inner tube.

15. The assisted lipectomy device of claim 14 wherein said limiting means comprises tab means attached to an outer surface of said inner tube, said tab means positioned within a groove in said handle.

16. The assisted lipectomy device of claim 9 further comprising:
a drive gear for engagement with said tube gear; and
a servomechanism coupled to said drive gear for alternately rotating said drive gear clockwise and counterclockwise, said drive gear and said servomechanism located within said handle.

17. An assisted lipectomy device comprising:
a handle having first and second ends and a cavity extending from said first end to said second end, and having a port at said second end for attachment to a vacuum source, said handle further having a groove along an inner surface near said first end;
an inner tube having distal and proximate ends and an outer surface, said proximate end of said inner tube being in fluid communication with said cavity of said handle at said first end of said handle, said inner tube further having a spiral slot with rounded edges and a pinion surrounding said proximate end;
an outer tube having distal and proximate ends and surrounding said inner tube, said proximate end of said outer tube being attached to said first end of said handle and having a longitudinal slot with rounded edges;
a flexible steel cable having first and second ends;
a motor remote from said handle, said motor rotatably driving said first end of said cable;
a rack coupled to said second end of said cable, said rack engaging said pinion whereby lateral movement of said rack causes rotational movement of said pinion; and a tab attached to said outer surface of said inner tube near said proximate end thereof, said tab slidably mating with said groove in said handle.

18. The assisted lipectomy device of claim 17 wherein said second end of said cable is attached to a cam disk, said second end of said cable being generally perpendicular to said cam disk, said cam disk being generally parallel to said rack, said cam disk having a lobe along its periphery, said rack slidably engaging said periphery of said cam disk, and further including means for biasing said rack toward said cam disk whereby, as said cam disk rotates, said rack oscillates laterally and said pinion and said inner tube oscillate rotationally.

19. The assisted lipectomy device of claim 17 wherein said second end of said cable is attached to an essentially circular disk, said second end of said cable being generally perpendicular to said circular disk, and said circular disk being generally parallel to said rack, said rack further being pivotally connected to the periphery of said circular disk.

* * * * *